(12) United States Patent
von dem Bussche-Hünnefeld et al.

(10) Patent No.: US 6,365,758 B1
(45) Date of Patent: Apr. 2, 2002

(54) PREPARATION OF TOCOPHERAL CARBOXYLATES OR TOCOTRIENYL ESTERS BY ACID-CATALYZED REACTION WITH CARBOXYLIC ACIDS

(75) Inventors: Joanna Linda von dem Bussche-Hünnefeld, Lampertheim; Hagen Jaedicke; Guido Harms, both of Ludwigshafen; Harald Laas, Maxdorf, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/013,813

(22) Filed: Jan. 26, 1998

(30) Foreign Application Priority Data

Feb. 7, 1997 (DE) .......................... 197 04 619

(51) Int. Cl.⁷ ............................................ C07D 311/04
(52) U.S. Cl. ...................................................... 549/410
(58) Field of Search .................................. 549/405, 410

(56) References Cited

U.S. PATENT DOCUMENTS 5,545,407 A   8/1996   Hall et al. ................... 424/401

FOREIGN PATENT DOCUMENTS

| DE | 1 035 960 | 8/1958 |
| EP | 0 313 303 B1 | 4/1989 |
| GB | 918954 | 2/1963 |
| WO | WO 97/28151 | 8/1997 |

OTHER PUBLICATIONS

Hans– Dieter. Jakube, et al., "Chemie", VEB F.A. Brockhaus Verlag Leipzig, 5 ed., vol. 2/L–Z, 1987, pp. 846–847.
R. P. Evstigneeva, et al., "Synthesis of Biologically Active Esters of Vitamin E (α–Tocopherol)", Izvestiya vysshikh uchebnykh zavedenii, Khimiya i khimicheskaya tekhnologiya, 1991, 34, (11), pp. 3–26.

Primary Examiner—Amelia Owens

(74) Attorney, Agent, or Firm—Oblon, Spivak, McClelland, Maier & Neustadt, P.C.

(57) ABSTRACT

A process for preparing tocopheryl esters or tocotrienyl esters by acid-catalyzed esterification of a tocopherol or a tocotrienol in a solvent while stirring at elevated temperature, which comprises a) carrying out the esterification with the appropriate carboxylic acid, b) carrying out the esterification with from 2.5 to 6 mol of the carboxylic acid in an aliphatic, cycloaliphatic or aromatic hydrocarbon boiling in the range from 80 to 200° C., or else with from 1.0 to 2.5 mol of the carboxylic acid in a mixture consisting of an aliphatic or cycloaliphatic hydrocarbon boiling in the range from 80 to 200° C. and a cyclic carbonate of the formula II or a γ-lactone of the formula III

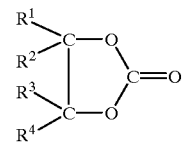
(II)

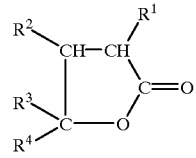

(III)

where $R^1$, $R^2$ and $R^3$ are each H or lower alkyl, and $R^4$ is H, lower alkyl, phenyl or methoxymethyl, as solvent, c) using a nonoxidizing strong inorganic or organic acid, preferably sulfuric acid, boroxalic acid or benzene- or toluenesulfonic acids, in catalytic amounts as acid catalyst, and d) continuously removing the water formed in the reaction by azeotropic distillation during the reaction.

11 Claims, No Drawings

PREPARATION OF TOCOPHERAL CARBOXYLATES OR TOCOTRIENYL ESTERS BY ACID-CATALYZED REACTION WITH CARBOXYLIC ACIDS

BACKGROUND OF THE INVENTION

The invention relates to a process for preparing tocopheryl esters or tocotrienyl esters by acid-catalyzed esterification of a tocopherol or a tocotrienol in a solvent at elevated temperature with the appropriate carboxylic acid, in particular with sorbic acid.

A tocopherol means according to the invention a compound of the formula I

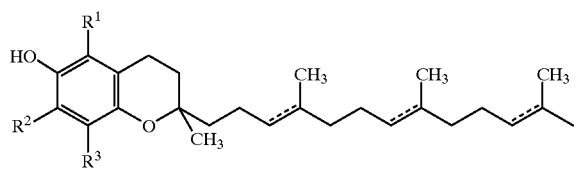

(I)

where $R^1$ to $R^3$ are H or methyl, and the side chain is saturated, and a tocotrienol is a corresponding compound in which the dotted lines denote another bond.

The process is of particular interest for preparing carboxylic esters of α-tocopherol, i.e. a compound where $R^1$ to $R^3$ are each methyl, and the side chain is saturated. α-Tocopherol has the highest vitamin E activity.

α-Tocopherol (vitamin E; VE) has recently attained great importance in livestock nutrition and as food supplement since it is the principal lipid-soluble biological antioxidant, and because of its additional biological effect. Since free tocopherols are very readily oxidized in air, they are preferably used in the form of their esters with carboxylic acids, which are relatively stable to atmospheric oxygen at room temperature. As is evident from formula I, tocopherols are compounds with a sterically hindered phenolic hydroxyl group and thus a hydroxyl group which is extremely difficult to esterify.

It is known about phenols themselves that although they react well with acid chlorides or anhydrides they do not react with carboxylic acids to give phenol esters (cf. Brockhaus Chemie, VEB F. A., Brockhaus Verlag Leipzig, 5th edition, 1987, Volume 2/L–Z, page 846–847, left-hand column, paragraph 3 or DBP 10 35 960). The same applies a fortiori to topopherols and tocotrienols with their sterically hindered OH group. Thus, the most important tocopheryl ester, tocopheryl acetate, is prepared industrially exclusively by reacting tocopherol with acetic anhydride.

A review of processes for preparing esters of α-tocopherol with aliphatic or aromatic carboxylic acids is to be found in Izvestiya vysshikh uchebnykh zavedenii, Khimiya i khimicheskaya tekhnologiya, 1991, 34(11), 3–26, in particular 4–9. According to pages 4–5 of loc. cit., alkyl carbonates are prepared by reacting VE with phosgene and subsequently with alkanols in the presence of pyridine or by reacting VE with acid chlorides of the alkylcarboxylic acids. According to page 5 of loc. cit., the palmitate, stearate, propionate, caprate and p-nitrobenzoate are also prepared by reacting VE with the appropriate acid chlorides in the presence of pyridine at 50 to 62° C. Although, according to page 5 of loc. cit., the palmitate and stearate can also be prepared by reacting VE with palmitic acid or stearic acid, this is only in the presence of costly exotic condensing agents such as carbonyldiimidazoles or thionyldiimidazoles. According to the foot of page 5 of loc. cit., succinates, malonates, glutarates and phthalates are prepared by reacting VE with a Grignard reagent and subsequently with anhydrides of the appropriate acids. According to page 6 of loc. cit., the malonate and phthalate are prepared by reacting VE with malonic anhydride and phthalic acid, respectively, in the presence of large amounts of $ZnCl_2$ as dehydrating agent. According to page 8 of loc. cit., α-tocopheryl methoxypolyoxyethyleneacetate is prepared by reacting VE with methoxypolyoxyethyleneacetic anhydride in the presence of p-toluenesulphonic acid (6 h) or in pyridine (6 days). According to page 8 of loc. cit., α-tocopheryl p-chlorophenoxyisobutyrate, which has antiatherosclerotic activity, is prepared by reacting VE with p-chlorophenoxybutyric acid in the presence of costly carbonyldiimidazoles or with the appropriate acid chloride in the presence of pyridine or else by reacting VE with sodium methoxide in methanol and reacting the resulting sodium salt of VE with p-chlorophenoxyisobutyryl chloride. According to page 8 of loc. cit., α-tocopheryl pivalate is prepared by condensing VE with pivalic acid in the presence of large amounts of pyrophosphate or under the influence of enzymes. According to the foot of page 8 of loc. cit., tocopheryl salicylate is prepared by condensing VE with salicylic acid in the presence of large amounts of tetraalkyl pyrophosphate. According to the top of page 9 of loc. cit., α-tocopheryl cinnamate and α-tocopheryl ferulate are prepared by reaction of the appropriate acid chlorides.

According to page 9 of loc. cit., the α-tocopheryl esters of linoleic acid, oleic acid and arachidonic acid, which are in demand as compounds with antiatherosclerotic effect, are prepared by reacting VE with said acids and acid chlorides or anhydrides of said acids in the presence of large amounts of tetraalkyl pyrophosphate or other acid scavengers or else recently by reacting VE with the appropriate acids in the presence of costly carbonyldiimidazoles or thionyldiimidazoles.

Another α-tocopheryl derivative of medical interest is α-tocopheryl sorbate which is of interest as sunscreen agent. It is prepared as disclosed in EP 313 303 B1 by reacting 1 mol of VE with 4.3 mol of a polyphosphate ester and subsequently stirring with 1 mol of sorbic acid for 16 hours.

Another application described for tocopheryl sorbate is its use as ingredient of dermatological compositions for anti-acne treatment (cf. U.S. Pat. No. 5,545,407).

As is evident from the cited prior art, α-tocopheryl esters are mostly prepared in the prior art by reacting VE with carbonyl chlorides or carboxylic anhydrides. The disadvantages of this are that the acid chlorides or anhydrides must previously be prepared in an elaborate manner, that working with acid chlorides industrially is rather costly, and that it is necessary in many cases to operate in pyridine, which is not advantageous for vitamin derivatives because of its unpleasant properties (inter alia the odor).

In the cases where VE is esterified with the carboxylic acids themselves in the prior art, it is necessary also to use multiple molar amounts of dehydrating agents such as polyphosphate esters, tetraalkyl pyrophosphate or zinc chloride or else to have costly condensing agents such as carbonyldiimidazoles or thionyldiimidazoles present. The use of polyphosphate esters and tetraalkyl pyrophosphate is unsuitable on an industrial scale because of the costly preparation thereof. As is evident from EP 313 303, for example, there are technical problems in preparing polyphosphate esters owing to the use of the very hygroscopic $P_2O_5$, the hazardous diethyl ether and chloroform, and the long reaction time of 48 hours. Use of zinc chloride and the imidazoles containing chloride ions from their preparation makes severe demands on the reactor material and results in high costs.

It is an object of the present invention to develop a process for esterifying tocopherols and tocotrienols in which the tocopherols or tocotrienols can be esterified with the appropriate carboxylic acids in a simple and industrially worthwhile manner without the need also to use a large excess of dehydrating agent or else costly exotic condensing agents such as carbonyldiimidazole or thionyldiimidazoles.

SUMMARY OF THE INVENTION

We have found that this object is achieved by a process for preparing tocopheryl esters or tocotrienyl esters by acid-catalyzed esterification of a tocopherol or a tocotrienol in a solvent while stirring at elevated temperature, which comprises a) carrying out the esterification with the appropriate carboxylic acid, b) carrying out the esterification with from 2.5 to 6 mol. preferably 3 to 5 mol. of the carboxylic acid in an aliphatic, cycloaliphatic or aromatic hydrocarbon boiling in the range from 80 to 200° C., preferably 110 to 130° C., or else with from 1.0 to 2.5 mol, preferably 1 to 1.5 mol, of the carboxylic acid in a mixture consisting of an aliphatic or cycloaliphatic hydrocarbon boiling in the range from 80 to 200° C. and a cyclic carbonate of the formula II or a γ-lactone of the formula III

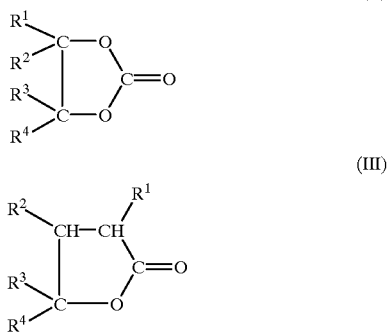

where $R^1$, $R^2$ and $R^3$ are each H or $C_1$–$C_4$–alkyl, and $R^4$ is H, $C_1$–$C_4$–alkyl, phenyl or methoxymethyl, as solvent, c) using a nonoxidizing strong inorganic or organic acid, preferably sulfuric acid, boroxalic acid or benzene- or toluenesulfonic acids, in catalytic amounts as acid catalyst, and d) continuously removing the water formed in the reaction by azeotropic distillation during the reaction.

Surprisingly, the cyclic carbonate and the γ-lactone remain stable under the reaction conditions and are not lost.

Examples of carboxylic acids which can be esterified with a tocopherol or tocotrienol by the process according to the invention are:

acetic acid, propionic acid, 1-n-hexanoic acid, caproic acid, sorbic acid, palmitic acid, stearic acid, oleic acid, linoleic acid and arachidonic acid.

The process according to the invention is of particular interest for reacting a tocopherol or a tocotrienol with acetic acid, propionic acid, sorbic acid, palmitic acid, stearic acid, oleic acid or linoleic acid as carboxylic acid.

It is possible to use as acid catalyst for the esterification reaction according to the invention a nonoxidizing strong inorganic or organic acid, ie. an acid with a $pK_a$ of about –6 to 3. Examples of particularly suitable acids are sulfuric acid, boroxalic acid (ie. an approximately equimolar mixture of boric acid and oxalic acid), a toluenesulfonic acid or a benzenesulfonic acid. The acids are generally used in amounts of from 0.001 mol to 0.2 mol of catalyst acid per mole of tocopherol or tocotrienol. The process according to the invention is particularly advantageous on use of from 0.004 to 0.1 mol of sulfuric acid as acid catalyst per mole of tocopherol or tocotrienol for the esterification.

Aliphatic hydrocarbons boiling in the range from 80 to 200° C., preferably 110 to 130° C., which can be employed according to the invention and which may be mentioned are heptanes and octanes, in particular n-heptane or mixtures of hydrocarbons such as hexanes, heptanes, octanes and/or nonanes.

A cycloaliphatic hydrocarbon which may be mentioned as suitable for the process according to the invention is cyclohexane.

Aromatic hydrocarbons which may be mentioned as suitable for use in a one-phase system are benzene and toluene. If only hydrocarbons, ie. a one-phase system, are used as solvents, it is necessary in most cases to use a large molar excess of the carboxylic acid. The carboxylic acid is then advantageously used in amounts of about 3 to 5 mol of carboxylic acid per mole of tocopherol or tocotrienol. The water formed in the esterification reaction can be continuously removed by azeotropic distillation with the aid of the hydrocarbon used as solvent, and can be removed in a water trap. The excess carboxylic acid can, e.g. in the case of sorbic acid, be removed by crystallization after the reaction is complete and the reaction mixture has cooled.

On use of a two-phase mixture consisting of an aliphatic hydrocarbon and a 5-membered cyclic carbonate of the formula II or a γ-lactone of the formula III for the esterification according to the invention it is generally necessary to employ the carboxylic acid only in equimolar amounts or else in a slight excess (up to about 100 mol % excess).

On use of mixtures consisting of a suitable hydrocarbon and a 5-membered cyclic carbonate or 5-membered lactone the water formed in the esterification is removed by distillation in a ternary azeotropic mixture. The lower phase in the fitted water trap then contains the water in the form of a solution in the carbonate or the γ-lactone and is removed, and the hydrocarbon is allowed to flow back continuously into the reaction vessel. The 5-membered cyclic carbonate or γ-lactone which has distilled out must be continuously replaced by new, ie. anhydrous, carbonate or γ-lactone in the reaction vessel. A great advantage of this variant of the process is that there is no need to remove large excesses of carboxylic acids, and the resulting tocopheryl ester or tocotrienyl ester can be isolated in very pure form from the hydrocarbon solution which can be easily removed as upper phase. The 5-membered cyclic carbonate or γ-lactone in the lower phase can be used for further esterifications after workup.

The process according to the invention is very particularly important for preparing α-tocopheryl sorbate, which is in demand as sunscreen agent or for antiacne treatment, because the esterification of tocopherols with unsaturated carboxylic acids represents a particular problem. The all-E-tocopheryl sorbate which is of particular interest for cosmetic use can also be prepared very advantageously by the process according to the invention without isomerization of the double bonds in the tocotrienol moiety or in the sorbic acid moiety. The process according to the invention is, therefore, to be illustrated hereinafter by the esterification of VE with sorbic acid.

Tocopheryl sorbate can advantageously be prepared by the process according to the invention when a) 2.5 to 6, preferably 4 to 5, mol of sorbic acid are used per mole of tocopherol for the esterification of VE, and b) the reaction is carried out at from 110 to 130° C. in a hydrocarbon boiling in the range from 80 to 200° C.

In the process according to the invention, it is advantageous to prepare essentially all-E-tocopheryl sorbate by a) using from 4.5 to 5.5 mol of sorbic acid per mole of all-E-tocopherol and b) carrying out the reaction at from 113° C. to 120° C. in petroleum spirit boiling in the range from about 80 to 140° C.

To isolate tocopheryl sorbate in this variant of the process it is advantageous to cool the reaction mixture after the esterification to from 0 to 5° C., and to filter off the excess sorbic acid which crystallizes out before working up the reaction mixture in a conventional way.

Another advantageous variant of the process according to the invention comprises preparing tocopheryl sorbate by a) using about 1.0 to 2.5 mol of sorbic acid per mole of tocopherol and b) carrying out the reaction in a mixture of an aliphatic or cycloaliphatic hydrocarbon boiling in the range from 80 to 200° C. and propylene carbonate or γ-butyrolactone.

The process according to the invention is very particularly advantageous when tocopheryl sorbate is prepared by a) using about 1.5 mol of sorbic acid per mole of tocopherol and b) carrying out the reaction in a mixture of octane and 1,2-propylene carbonate at about 110 to 130° C.

The procedure for this variant of the process is advantageously such that the tocopherol and the sorbic acid are introduced into the mixture of octane and 1,2-propylene carbonate or γ-butyrolactone, concentrated sulphuric acid is added dropwise as catalyst, then the reaction mixture is refluxed for from 3 to about 15 hours, with the water formed in the reaction being removed by azeotropic distillation and being continuously separated out in the form of a solution in propylene carbonate or γ-butyrolactone which results as lower phase from the condensate collected in a trap and the propylene carbonate or γ-butyrolactone being replaced by anhydrous propylene carbonate or γ-butyrolactone, and where finally the required tocopheryl sorbate is isolated from the octane phase in a conventional way.

The following examples are intended to illustrate the process according to the invention.

EXAMPLE 1

228 g (0.496 mol) of d,l-α-tocopherol (purity>96%) and 278 g (2.48 mol) of all-E sorbic acid were dissolved in 1.5 l of petroleum spirit boiling in the range from 100 to 140° C. in a 4:1 scale up vessel with anchor stirrer and, while stirring vigorously (200 rpm), 5 g (about 0.05 mol) of concentrated (conc.) sulfuric acid were added dropwise to this over the course of 10 minutes (min). The reaction mixture was then refluxed in heating oil at 145° C. (internal temperature about 110 to 120° C.) with azeotropic removal of water (W) for 9 hours (h). The content of unreacted tocopherol determined by gas chromatography (GC) after this time was 1 to 1.5%.

The reaction mixture was then cooled to 0 to 5° C., the excess sorbic acid which crystallized out was filtered off, and the resulting filtrate was worked up further. This was done by first adding 100 ml of W, adjusting to pH 7–8 with 18 ml of 25% strength sodium hydroxide solution, and subsequently separating the phases, preventing emulsion formation from the outset by cautious washing. Then the basic wash was followed by two washes with 500 ml of W each time, and subsequently the organic phase was concentrated to result in a dark brown oil. This was further purified by molecular distillation at 200 to 209° C. under 0.03 to 0.05 bar. This distillation reduced the free tocopherol content to <1%.

The yield of pale yellow all-E-α-tocopherol sorbate was 81% of theory based on tocopherol.

EXAMPLE 2

Pilot-plant example with 3 equivalents of sorbic acid 33.3 kg (77.3 mol) of d,l-α-tocopherol (purity>96%) and 25.2 kg (224.7 mol) of all-E-sorbic acid were dissolved in 150 l of petroleum spirit boiling at 100–140° C. in a 250 liter enameled steel pilot-plant vessel with anchor stirrer and, while stirring (1/80 min), heated to reflux (internal temperature about 110–115° C.), 0.78 kg (7.96 mol) of conc. sulfuric acid was added dropwise to the reaction mixture over the course of 1 h, and the mixture was kept at this temperature with azeotropic removal of W for 15 h. The content of unreacted tocopherol determined by GC after this time was 4.5 to 5%.

The reaction mixture was then cooled to −5 to +5° C., the excess sorbic acid which crystallized out was filtered off, and the resulting filtrate was worked up further.

This was done by first adjusting to pH 7–8 with 40 l of W and 2.95 l of a 25% by weight sodium hydroxide solution, and subsequently separating the phases. The basic wash was followed by two further washes with W and subsequent phase separation. The organic phase was concentrated in a thin film evaporator to result in a dark brown oil. This was further purified by molecular distillation at 210–220° C. under about 0.01 mbar. The distillation resulted in a transparent yellow oil with a tocopheryl sorbate content of >96% and a free tocopherol content below 2%. The yield after distillation was about 80% of theory.

EXAMPLE 3

22.4 g (0.05 mol) of d,l-α-tocopherol and 8.8 g (0.08 mol) of all-E-sorbic acid were dissolved in a mixture of 100 ml of 1,2-propylene carbonate and 100 ml of n-octane and, after addition of 4 drops of conc. sulfuric acid, the resulting mixture was refluxed (internal temperature 125° C.) for 12 h. During this esterification, the lower phase of propylene carbonate and W which separated out in the water trap was continuously removed, while the octane continuously flowed back into the reaction vessel. The removed propylene carbonate was continuously replaced by anhydrous material. The ratio of tocopherol to tocopheryl sorbate after the 12 h according to HPLC (100% methanol as eluant, UV detector at 280 nm, $C_{30}$ column) was 3/97.

The mixture was cooled to room temperature (RT), the upper phase was separated off, this octane phase was washed with dilute sodium carbonate solution and W, and the octane was distilled off under reduced pressure to result in 24.8 g of pure all-E-tocopheryl sorbate, corresponding to a yield of 91% of theory.

EXAMPLE 4 a) Reaction of d,l-α-tocopherol with 1+1 mol of sorbic acid per mol of tocopherol in octane/1,2-propylene carbonate 22.4 g (0.05 mol) of pure d,l-α-tocopherol in a mixture of 100 ml of octane and 100 ml of 1,2-propylene carbonate were heated to 100° C., and then 5.83 g (0.05 mol) of pure sorbic acid and 2 drops of conc. sulfuric acid were added. The mixture was subsequently heated rapidly to an internal temperature of 125° C. and then water-containing solvent mixture was slowly distilled over the course of 5 h into a phase separator, during which the nonpolar octane upper phase flowed continuously back into the reaction vessel, while the polar lower phase consisting of W and propylene carbonate was separated off, collected and worked up. The amount of propylene carbonate distilled off was continuously replenished in the reaction vessel by fresh anhydrous propylene carbonate. Portions of 2.9 g (0.025 mol) of pure sorbic acid were added to the reaction mixture after reaction for 1 h and after a further h. The reaction was followed by HPLC analysis:

| Reaction time [h] | Tocopherol [% area] | Sorbate [% area] | Remarks |
|---|---|---|---|
| 1 | 36 | 64 | +2.5 g of sorbic acid |
| 2 | 17 | 83 | +2.5 g of sorbic acid |
| 3 | 5 | 95 | |
| 4 | 1.4 | 98.6 | |
| 5 | 1 | 99 | |

After a total of 5 h, the mixture was cooled to RT, and the phases were separated. The lower phase was washed with 50 ml of octane, and the combined octane phases were then washed with 100 ml of a 5% by weight aqueous sodium carbonate solution, 100 ml of 5% by weight aqueous acetic acid and 100 ml of W. After drying over $MgSO_4$, the octane was distilled off, and then the residue was distilled in a thin film evaporator at 200° C./0.01 mbar to result in 22.96 g of pure d,l-α-tocopheryl sorbate. This corresponds to a yield of 84% of theory.

b) for comparison

Reaction of d,l-α-tocopherol with 1+1 mol of sorbic acid per mol tocopherol in octane.

The procedure was as described as under a) but only 200 ml of octane were used in place of the mixture of 100 ml of octane and 100 ml of 1,2-propylene carbonate described therein. The tocopherol conversion was followed by HPLC analysis in this case too:

| Reaction time [h] | Tocopherol [% area] | Tocopheryl sorbate [% area] | Remarks |
|---|---|---|---|
| 1 | 80 | 20 | +2.9 g of sorbic acid |
| 2 | 73 | 27 | +2.9 g of sorbic acid |
| 3 | 63 | 37 | |
| 4 | 55 | 45 | |
| 5 | 50 | 51 | |

The upper phase flowed continuously back into the reaction vessel, and about 0.5 ml of lower phase was discarded.

The reaction solution was subsequently washed twice with 200 ml of a 5% by weight sodium carbonate solution each time and then with 5% by weight aqueous acetic acid and W and was dried. The octane was distilled off to result in 23.1 g of a residue which consisted of 12.8 g of tocopherol and 10.3 g of topopheryl sorbate. It was not possible to separate the substances by distillation.

EXAMPLES 5, 6 AND 7

Esterification of tocopherol with sorbic acid, 1-n-hexanoic acid and oleic acid in octane/1,2-propylene carbonate In each case, 89.5 g (0.2 mol) of d,l-α-tocopherol (purity 98.5%) were introduced into a mixture of 400 ml of 1,2-propylene carbonate and 500 ml of octane. About 100 ml of octane were distilled off, and 0.2 mol of the carboxylic acid evident from the following Table, and the acidic catalyst evident from the Table, in the amount indicated in the Table, were added. After heating to the internal temperature indicated in the Table, a water/octane/propylene carbonate mixture was slowly distilled out into a phase separator. The nonpolar octane upper phase ran continuously back from the phase separator into the reaction vessel, while the lower phase containing water and propylene carbonate was collected for working up. Dry propylene carbonate was introduced into the reactor at the rate at which propylene carbonate distilled out. A further 0.1 mol of the carboxylic acid indicated in the Table was added 2 h after the start of the reaction.

After the reaction time indicated in the Table, the reaction mixture was cooled, the phases were separated, and the lower phase was extracted with 200 ml of octane. The octane phases were washed as described above with 5% by weight sodium carbonate solution (with 4% by weight sodium hydroxide solution in Examples 6 and 7), dilute acetic acid and W and were distilled. The yields are indicated in the following Table.

TABLE

| Example | Carboxylic acid | Catalyst | Reaction temperature [° C.] | Reaction time [h] | Tocopheryl ester (Yield) [g] |
|---|---|---|---|---|---|
| 5 | Sorbic acid 23.4 g +11.6 g* | conc. $H_2SO_4$ 0.5 g | 126 | 8 | Tocopheryl sorbate** (pale yellow clear viscous oil; purity 99%) 94.2 g |
| 6 | 1-n-Hexanoic acid 24.2 g +12.1 g* | Boroxalic acid**** 8 g | 128 | 5 | Tocopheryl hexanoate** 101.2 g |
| 7 | Oleic acid 59.2 g +30.0 g* | Boroxalic acid**** 8 g | 128 | 12 | Tocopheryl oleate 118.2 g*** |

*after reaction for 2 h
**after distillation in short-path evaporator
***after filtration of the octane phase through a thin layer of silica gel and removal of the octane by distillation.
****Mixture of 6 g of oxalic acid and 2 g of boric acid.

EXAMPLE 8

Esterification of tocopherol with palmitic acid 22.4 g of d,l-α-tocopherol were heated together with 100 ml (120 g) of 1,2-propylene carbonate and 100 ml of octane to 125° C. Then 13.3 g (0.05 mol) of palmitic acid and 2 g of boroxalic acid, ie. a mixture of 0.5 g of boric acid and 1.5 g of oxalic acid, were added, and a water-containing azeotrope was slowly distilled out. While the nonpolar octane upper phase continuously flowed back into the reaction vessel, the aqueous propylene carbonate lower phase was collected separately for workup. The amount of propylene carbonate distilled out was continuously replaced in the reaction vessel.

1 h after the start of the reaction, a further 6.7 g (0.025 mol) of palmitic acid was added, and distillation was continued. After 7 h, 97% of the tocopherol had been converted into the palmitate.

The mixture was cooled, the phases were separated, and the polar lower phase was washed with 50 ml of octane. The combined octane phases were washed with 5% by weight sodium carbonate solution, methanol, 5% by weight acetic acid and W and were dried. The octane was distilled off to result in 29.8 g of a rapidly solidifying oil consisting of pure tocopheryl palmitate containing only 0.8 g of unesterified tocopherol.

EXAMPLE 9

11.1 g of pure d,l-α-tocopherol were dissolved in a mixture of 75 ml of 1,2-propylene carbonate and 75 ml of n-heptane. The solution was heated to an internal temperature of 102° C. and then 6 g of acetic acid and 2 drops (about 0.11 g) of conc. sulfuric acid were added. The mixture was heated while slowly distilling out an azeotropic mixture of water, n-heptane and propylene carbonate, the heptane being continuously returned from the phase separator to the reaction vessel, while the lower phase containing water and propylene carbonate was collected for workup, and dry propylene carbonate was metered into the reaction vessel at the same rate as propylene carbonate distilled out of the reaction mixture.

After 12 h, 98% of the tocopherol were esterified. The mixture was cooled to RT, the heptane upper phase was separated off and washed twice with dilute sodium carbonate solution, the heptane was distilled off, and the residue was fractionated under high vacuum.

9.1 g of pure tocopheryl acetate were obtained.

We claim:

1. A process for preparing tocopheryl esters or tocotrienyl esters, comprising:
   a) carrying out esterification of a tocopherol or a tocotrienol with from 2.5–6 mol of a carboxylic acid in an aliphatic, cycloaliphatic or aromatic hydrocarbon boiling in the range of 80–200° C., or else with from 1.0–2.5 mol of the carboxylic acid in a two-phase mixture consisting of an aliphatic or cycloaliphatic hydrocarbon boiling in the range of 80–200° C. and a cyclic carbonate of formula II or a γ-lactone of formula III

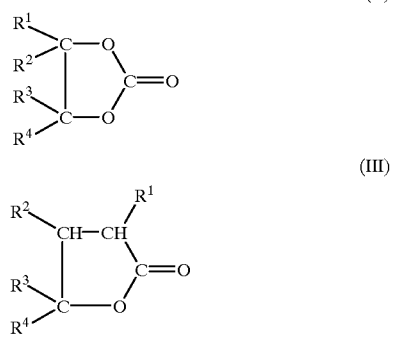

wherein $R^1$, $R^2$ and $R^3$ are each H or $C_{1-4}$-alkyl and $R^4$ is H, $C_{1-4}$-alkyl, phenyl or methoxymethyl, as the solvent, in the presence of a nonoxidizing strong inorganic or organic acid catalyst employed in catalytic amounts; and
   b) continuously removing the water formed in the reaction by azeotropic distillation during the reaction.

2. The process as claimed in claim 1, wherein the tocopherol reactant is esterified with acetic acid, propionic acid, 1-n-heptanoic acid, sorbic acid, palmitic acid, stearic acid, oleic acid or linoleic acid.

3. The process as claimed in claim 1, wherein said acid catalyst is sulfuric acid, boroxalic acid or benzene- or toluenesulfonic acid.

4. The process as claimed in claim 1, wherein the boiling range of said aliphatic, cycloaliphatic or aromatic hydrocarbon solvent ranges from 110–130° C.

5. The process as claimed in claim 1, wherein a tocopheryl sorbate is prepared by:
   i) reacting a tocopherol with from 2.5–6 mol of sorbic acid per mol of said tocopherol at a temperature ranging from 110–130° C. in a hydrocarbon boiling in the range from 80–200° C.

6. The process as claimed in claim 5, wherein an all-E-tocopherol sorbate is prepared by:
   i) reacting a tocopherol with from 4.5–5.5 mol of sorbic acid per mol of tocopherol at a temperature ranging from 113–120° C. in petroleum spirits boiling in the range of from 80–140° C.

7. The process as claimed in claim 5, which further comprises:
   i) after said esterification reaction, cooling the reaction mixture to 0–5° C., thereby achieving the precipitation of excess sorbic acid as crystals which are filtered from the reaction mixture.

8. The process as claimed in claim 6, which further comprises:
   i) after said esterification reaction, cooling the reaction mixture to 0–5° C., thereby achieving the precipitation of excess sorbic acid as crystals which are filtered from the reaction mixture.

9. The process as claimed in claim 1, wherein a tocopheryl sorbate is prepared by:
   i) reacting a tocopherol with about 1.0–2.5 mol of sorbic acid per mol of said tocopherol in a solvent mixture of an aliphatic or cycloaliphatic hydrocarbon boiling in the range of 80–200° C. and propylene carbonate or γ-butyrolactone.

10. The process as claimed in claim 1, wherein a tocopheryl sorbate is prepared by:
    i) reacting a tocopherol with about 1.5 mol of sorbic acid per mol of said tocopherol in a solvent mixture of heptane or octane and propylene carbonate or γ-butyrolactone at a temperature of 100–150° C.

11. The process as claimed in claim 10, wherein:
    i) said tocopherol and sorbic acid are introduced into the solvent mixture of heptane or octane and 1,2-propylene carbonate or γ-butyrolactone, with the addition of concentrated sulfuric acid by the dropwise addition of the catalyst to the solvent mixture, followed by refluxing the reaction medium for about 5 to about 15 hours;
    ii) the water formed during the reaction being removed by azeotropic distillation with the propylene carbonate or γ-butyrolactone component of the solvent which separates as the lower phase of a solvent condensate collected in a trap for the reaction, the propylene carbonate or γ-butyrolactone component of the reaction solvent being replaced by the addition of anhydrous propylene carbonate or γ-butyrolactone to the reaction medium; and
    iii) isolating the tocopheryl sorbate product from the heptane or octane component of the reaction medium.

* * * * *

UNITED STATES PATENT AND TRADEMARK OFFICE
CERTIFICATE OF CORRECTION

PATENT NO.     : 6,365,758 B1                                                              Page 1 of 1
DATED          : April 2, 2002
INVENTOR(S)    : von dem Bussche-Hünnefeld et al.

It is certified that error appears in the above-identified patent and that said Letters Patent is hereby corrected as shown below:

<u>Title page, Item [54] and Column 1, lines 1-4,</u>
The Title should read as follows:
-- [54]  THE PREPARATION OF TOCOPHERYL CARBOXYLATES OR TOCOTRIENYL ESTERS BY ACID-CATALYZED REACTION WITH CARBOXYLIC ACIDS --

<u>Title page,</u>
Item [75], the Inventors should read as follows:
-- [75]  Inventors:  Joanna Linda von dem Bussche-Hünnefeld, Lampertheim; Hagen Jaedicke, Ludwigshafen; Guido Harms, Limburgerhof; Harald Laas, Maxdorf, all of (DE) --

Signed and Sealed this

First Day of October, 2002

Attest:

Attesting Officer

JAMES E. ROGAN
*Director of the United States Patent and Trademark Office*